United States Patent
Griffin

(10) Patent No.: US 10,413,362 B2
(45) Date of Patent: Sep. 17, 2019

(54) MULTIWAVELENGTH SURGICAL LASER

(71) Applicant: InnovaQuartz LLC, Phoenix, AZ (US)

(72) Inventor: Stephen E. Griffin, Peoria, AZ (US)

(73) Assignee: InnovaQuartz Inc., Phoenix, AZ (US)

( * ) Notice: Subject to any disclaimer, the term of this patent is extended or adjusted under 35 U.S.C. 154(b) by 100 days.

(21) Appl. No.: 14/945,053

(22) Filed: Nov. 18, 2015

(65) Prior Publication Data

US 2016/0184019 A1  Jun. 30, 2016

Related U.S. Application Data

(62) Division of application No. 14/584,086, filed on Dec. 29, 2014, now Pat. No. 9,220,563.

(51) Int. Cl.
*A61B 18/20* (2006.01)
*A61B 18/22* (2006.01)
(Continued)

(52) U.S. Cl.
CPC .............. *A61B 18/22* (2013.01); *A61B 18/20* (2013.01); *A61B 2018/00547* (2013.01); *A61B 2018/00577* (2013.01); *A61B 2018/00589* (2013.01); *A61B 2018/00601* (2013.01); *A61B 2018/00625* (2013.01); *A61B 2018/1807* (2013.01); *A61B 2018/207* (2013.01); *A61B 2018/208* (2013.01); *A61B 2018/2015* (2013.01); *A61B 2018/2035* (2013.01); *A61B 2018/2065* (2013.01); *A61B 2018/2205* (2013.01); *A61B 2018/2244* (2013.01)

(58) Field of Classification Search
CPC ....... A61B 18/20; A61B 18/22; A61B 18/201; A61B 2018/2025; A61B 2018/203; A61B 2018/2035; A61B 2018/2065; A61B 2018/207; A61B 2018/2075; A61B 2018/2211; A61B 2018/2255; A61B 2018/00547; A61B 2018/00571; A61B 2018/00577; A61B 2018/00589; A61B 2018/00595; A61B 2018/00601; A61B 2018/00607; A61B 2018/00619; A61B 2018/00625
USPC .................... 606/3–18; 607/88, 89; 128/898
See application file for complete search history.

(56) References Cited

U.S. PATENT DOCUMENTS

| | | |
|---|---|---|
| 4,573,465 A | 3/1986 | Sugiyama et al. |
| 4,641,912 A | 2/1987 | Goldenberg |
| (Continued) | | |

*Primary Examiner* — Ahmed M Farah

(57) ABSTRACT

A multiwavelength laser-based intense light source is described having applications in incision, excision and ablation of soft tissues with minimal collateral tissue damage. The light source combines the output of a plurality of relatively low power laser sources, emitting radiation in the region of the electromagnetic spectrum bounded by approximately 350 nm to 450 nm, where the combined output may be coupled into a single fiber optic energy delivery device: a standard surgical probe. Spectral and spatial beam combining are used to produce an incoherent light source with relatively low average power at any given wavelength, but with high total power and superior M2 beam quality, targeting multiple chromophores in target tissue and tissue breakdown product chromophores for consistently high and target absorption without indiscriminant char interference throughout a surgical procedure.

16 Claims, 5 Drawing Sheets

(51) Int. Cl.
    *A61B 18/00*      (2006.01)
    *A61B 18/18*      (2006.01)

(56) References Cited

U.S. PATENT DOCUMENTS

| | | | |
|---|---|---|---|
| 4,832,023 A * | 5/1989 | Murphy-Chutorian | ................ A61B 18/245 604/96.01 |
| 5,111,832 A | 5/1992 | Saksena | |
| 5,139,494 A | 8/1992 | Freiberg | |
| 5,144,630 A | 9/1992 | Lin | |
| 5,304,167 A * | 4/1994 | Freiberg | ................ A61B 18/24 606/10 |
| 5,387,211 A | 2/1995 | Saadatmanesh et al. | |
| 5,451,221 A * | 9/1995 | Cho | ................ A61B 18/24 606/14 |
| 5,540,676 A | 7/1996 | Freiberg | |
| 5,655,547 A | 8/1997 | Karni | |
| 5,746,735 A * | 5/1998 | Furumoto | ............ A61B 18/203 128/898 |
| 5,970,983 A | 10/1999 | Karni et al. | |
| 5,999,555 A | 12/1999 | Connors et al. | |
| 6,005,717 A | 12/1999 | Neuberger et al. | |
| 6,306,130 B1 | 10/2001 | Anderson et al. | |
| 6,385,221 B1 | 5/2002 | Neuberger | |
| 6,391,022 B1 | 5/2002 | Furumoto et al. | |
| 6,503,268 B1 | 1/2003 | Neuberger et al. | |
| 6,547,781 B1 | 4/2003 | Furumoto | |
| 6,554,824 B2 * | 4/2003 | Davenport | ............ A61B 18/22 600/2 |
| 6,986,764 B2 | 1/2006 | Davenport et al. | |
| 7,063,694 B2 | 6/2006 | Nahen et al. | |
| 8,784,461 B2 * | 7/2014 | Webb | ................ A61N 5/0618 607/88 |
| 2003/0109860 A1 * | 6/2003 | Black | ................ A61B 18/20 606/10 |
| 2004/0133191 A1 * | 7/2004 | Momiuchi | ............ A61B 18/20 606/10 |
| 2007/0100401 A1 * | 5/2007 | Lin | ................ A61B 18/203 607/89 |
| 2007/0185474 A1 | 8/2007 | Nahen | |
| 2007/0219601 A1 * | 9/2007 | Neuberger | ............ A61B 18/24 607/89 |
| 2010/0145191 A1 | 6/2010 | Jensen | |
| 2012/0071867 A1 | 3/2012 | Ryan et al. | |
| 2012/0143176 A1 | 6/2012 | Ryan et al. | |
| 2014/0350534 A1 * | 11/2014 | Kircher | ............ A61B 18/203 606/10 |
| 2016/0135892 A1 * | 5/2016 | Yu | ................ A61B 18/24 606/3 |

* cited by examiner

MULTIWAVELENGTH SURGICAL LASER

CROSS-REFERENCE

This disclosure claims the benefit of priority to U.S. patent application Ser. No. 14/584,086, filed Dec. 29, 2014, the disclosure of which is incorporated herein in its entirety.

FIELD OF THE INVENTION

A multiwavelength laser-based surgical device having applications in incision, excision and ablation of soft tissues with minimal collateral tissue damage.

BACKGROUND

Surgical "vaporization" of tissue, or "ablation", is simple as a physical concept but is chemically quite complex. While the dominant constituent of most human tissues is water and water does truly vaporize upon heating, the organic components (proteins, fats, nucleic acids, sugars) generally thermally decompose, or burn, before becoming vapor. Heat must be produced in tissue to vaporize water and decompose and then vaporize organic tissue components, but laser energy is not necessarily the source of all of the heat doing work in surgery; much of the energy involved derives from exothermic processes within the tissues that are stimulated by the laser energy, much as a match to a candle.

In soft tissues, laser radiation is converted to vibrational energy at some point during a cascade of simultaneous chemical reactions that take place. Even where chromophores strongly absorb the surgical laser wavelength, the local energy density is far below that required for photodissociation: target compounds absorb light and convert photonic energy into vibrational energy through electronic and phononic interactions. Some of the vibrational energy in chromophore(s) is also conducted (as heat) to adjacent compounds that absorb the incident laser radiation less efficiently than the primary chromophore(s). Where secondary species are in close proximity to primary chromophores, or are relatively volatile (e.g. water), they may decompose or vaporize rapidly. Where the thermal conduction path is longer, organic tissue components may be thermally damaged but not immediately removed (coagulation), which may increase post-operative complications and can even result in death; tissue coagulation is a complication of laser surgery in soft tissues that may result in hyponatremia and is to be avoided.

The efficiency of chromophore absorption, and the concentration of the chromophore, affects the depth of penetration of the incident laser light: given equivalent power density, the more concentrated the chromophore and more efficient the absorption, the shallower the light will penetrate a given tissue. Shallow penetration necessarily concentrates laser radiation in smaller tissue volumes and the underlying coagulation zones are concomitantly thin. At deep depths of penetration, significant volumes of tissue underlying the target tissue are irradiated at power densities insufficient for vaporization and are thus coagulated: a shallow depth of penetration exposes smaller underlying volumes of tissue to sub-therapeutic energy densities. Similarly, as laser power applied to target tissues is increased, the depth of penetration of damaging, sub-therapeutic energy also increases and more non-target tissue volume is coagulated. A laser wavelength that offers extremely high absorptivity in target tissues may be used at much higher average power with the same or less collateral tissue damage (coagulation) than a laser wavelength that is less efficiently absorbed.

For most surgical lasers, the target chromophore(s) is but a fraction of the tissue mass; where water is the chromophore it is a considerable fraction, but in that water is also a ubiquitous constituent of tissue, it is far from a tissue-specific target; labeling water a 'chromophore', in fact, is dubious given its broad absorption spectrum and lack of tissue specificity. Non-targeted tissue components absorb laser light less efficiently and less efficient absorption results in scattering of the incident beam. This more or less "non-specific absorption" also contributes to sub-optimal tissue heating and collateral tissue damage (coagulation) of adjacent and underlying tissues through thermal contact. Inefficient laser absorption by tissue breakdown products also leads to "charring": the carbonization of organic tissue components that is familiar to any backyard grilling enthusiast. In surgery, charred tissue scatters laser energy quite strongly and under mechanisms (and affects) that differ with the size (mean diameter) of the carbon particles and particle aggregates, adding to collateral tissue damage and rendering the final therapeutic outcome far less predictable.

Whether water and/or hemoglobin strongly absorb the laser energy has evolved as a discriminating characteristic for laser manufacturers in marketing campaigns (as well as in patent claims) and has spawned a new term—"photoselectivity"—a word that is used to infer unique precision in targeting a "specific" tissue component (hemoglobin or $H_2O$). Lasers that target water as the primary chromophore (e.g. NIR diodes, holmium, thulium, erbium) are deemed 'photoselective' for water in that most of the other tissue components do not absorb these lasers' wavelengths strongly (but all tissues contain water). Lasers said to be photoselective for hemoglobin, e.g. Greenlight HPS, are only photoselective for as long as hemoglobin exists in the target tissue—on the order of femtoseconds post initial exposure—after which these laser wavelengths affect tissues much the same as any other laser wavelength.

Concomitant with the desired laser-tissue interactions during laser surgery, simultaneous and undesirable processes occur that cause damage to non-target tissues and to the surgical fiber optic probe. Where the surgical goal is to affect vaporization of soft tissues, coagulation of adjacent and underlying tissues occurs to a greater or lesser extend depending upon the characteristics of the laser light used, e.g. wavelength, average power density, beam profile, instantaneous energy density, variable surgical expertise and the light absorption characteristics of the target tissue, e.g. concentration of chromophores, scattering centers, tissue density, thermal conduction. Coagulated and chemically altered tissues adhere to the surgical probe, absorbing energy intended for target tissues and heating the probe instead, often to temperatures that severely damage the probe and nearby tissues, i.e. up to temperatures resulting in incandescence and even melting of the fused silica probe tip.

At any power level of current visible and near infrared lasers used in ablating tissue, heat ultimately does the bulk of the work and causes the bulk of the problems. Ideally, this heat is confined to as small a tissue volume as possible during application of energy such that affected tissues are ablated and not merely coagulated, but inefficient delivery of even highly absorbed radiation by damaged surgical probes results in undesirable outcomes, e.g., generalized heating, that may cascade into even more undesirable outcomes.

Non-radiative relaxation heats the system (the tissue microenvironment) where radiative relaxation reintroduces photonic energy to the microenvironment. The complexity of the resulting microenvironment therefore increases as new vibrational states are created and photons of different energy are emitted. More complexity is introduced as chemical bonds break and form, creating new molecules that absorb and radiate energy differently than the untreated tissue. The intense laser irradiance in surgery brings forth additional phenomena such as non-linear absorption (multi-photon absorption) and saturable adsorption (loss of absorptivity due to saturation of excited states).

Char is formed from the carbonization of tissue and is thermally driven. Development of char on tissue during laser surgery is advocated for strongly absorbing visible and near IR wavelengths, purportedly improving surgical efficiency but it also increases coagulation and results in slower localized healing. In particular, carbon particles with a high refractive index scatter incident laser radiation to create higher collateral tissue damage. Two models of light scattering by carbon particles must be considered in describing the adverse scattering: Rayleigh and Mie scattering.

The Rayleigh scattering model applies to particles much smaller than the wavelength scattered. The scatter intensity increases as the ratio of particle size to wavelength increases, up to particle mean diameters of approximately 10% of the wavelength (after which the model breaks down). Rayleigh scatter is equally intense in forward and reverse directions but the overall intensity is small relative to the incident energy. As carbon particles grow in diameter past approximately 10% of the incident wavelength, Mie scattering comes to dominate. Mie scatter is very intense in comparison to Rayleigh scatter and it is proportional to the square of the particles' cross-sectional area—increasing exponentially with particle size—and forward scatter angles are favored. Accordingly, a small amount of char may improve tissue removal rates through Rayleigh scattering, initially, but as the particles grow to favor Mie scatter, collateral tissue damage increases much more rapidly than ablation efficiency; even a little char is undesirable.

A common chromophore 'targeted' by surgical lasers is oxyhemoglobin ($HbO_2$): the most abundant, true chromophore endogenous to most tissue. Surgical laser companies use the strong absorption of $HbO_2$ in rationalization of high performance for any laser wavelength that falls at, or relatively close to, even minor absorptivity peaks. In situ, laser induced changes in oxyhemoglobin include deoxygenation, loss of the heme-porphyrins and formation of free heme, denaturalization of the protein, thermal decomposition, etc. This laser induced chemistry proceeds very quickly and produces a blizzard of complex chemical reactions including coupling of N-terminal amino acids and reducing sugars, e.g. deoxyribose, Amadori and Maillard reactions, and ultimately carbonization.

The most successful soft tissue surgical laser to date is the $CO_2$ laser. Water, $HbO_2$ and most other tissue constituents strongly absorb the $CO_2$ laser wavelength of 10.6 μm (10, 600 nm) but flexible waveguides suitable for endosurgery applications, such as vaporization of hyperplastic prostate tissue, have proven elusive, limiting $CO_2$ laser applications in surgery primarily to external tissues, e.g. plastic surgery. Early laser treatment of benign prostatic hyperplasia (BPH) used Nd:YAG lasers and frequency doubled Nd:YAGs (aka KTP lasers at 532 nm) and silica optical fiber probes but owing to relatively deep penetration within the target tissue, the 1064 nm wavelength coagulated far more tissue than it vaporized and post-operative complication rates were high.

Beginning in the late 1990s, Ho:YAG lasers largely replaced Nd:YAG lasers for BPH surgery because the 2140 nm wavelength penetrates tissue much less than 1064 nm due to a strong absorption by water, but the pulse output of holmium lasers leaves ragged tissue edges while the wavelength and high peak pulse energies stress fiber optic surgical probes while strong absorption by water—also used in sterile irrigation of the surgical field—causes boiling at probe tips and strongly attenuates the laser energy unless the probe is maintained in close contact with the target tissue (where tissue contact is damaging to the surgical probe).

Frequency doubled Nd:YAG/KTP lasers reached 532 nm output powers capable of reasonably efficient vaporization by the early 2000s. Prostate tissue proved to absorb the "greenlight" fairly well while the laser energy passed through water unaffected, but the single $HbO_2$ target chromophore was found to "bleach" rapidly, greatly reducing vaporization efficiency as surgery progressed. Tm:YAG lasers appeared in the mid-2000s, offering a 2000 nm wavelength similar to the Ho:YAG, but continuous rather than pulsed with water strongly absorbing the energy: surgical probe to tissue separation issues remain similar to Ho:YAG.

High power diode lasers were presented as lower cost alternatives to the solid state lasers starting at 880 nm and progressing to 980 nm and 1470 nm while 532 nm laser output was increased twice in the next decade, from 80 W to 120 W and finally to 180 W. All of the infrared lasers then joined in the power race with a 980 nm/1470 nm dual wavelength diode laser producing 200 W of combined power (or 160 W at 980 nm and 40 W at 1470 nm, individually or blended, said to offer a continuum of tissue response from vaporization and coagulation), a 250 W diode laser at 980 nm, a Ho:YAG offering 120 W average power (pulsed) and a 200 W Tm:YAG.

Alone, higher power lasers present diminishing returns, particularly for wavelengths that target $HbO_2$, the higher power caused photobleaching of the target tissue and significantly reduced hemostasis (i.e., more bleeding with more power). While high power lasers cause deeper coagulation, they increase expenditures due to consumption of the surgical fibers used to deliver the laser energy to, for example, the prostate. Notably, higher laser powers consume fibers more quickly or require larger, more expensive optical fiber, e.g. a 532 nm laser at 80 W or 120 W requires a 600 μm core fiber whereas at 180 W requires a liquid-cooled 750 μm core fiber.

SUMMARY

A multiwavelength surgical tool comprising: a first plurality of laser sources: each laser source, individually, having an output wavelength in the range of about 340 nm to about 460 nm, preferably 380-440, and each laser source output wavelength, individually, corresponding to an absorption maximum of an endogenous chromophore in the range of about 340 nm to about 460 nm, their bathochromatic and hypsochronatic shift maxima, absorption maxima of their breakdown products and recombination products thereof; and the plurality of laser sources optically coupled to an interventional or diagnostic surgical-laser-delivery device.

A surgical process comprising: combining a plurality of narrow-wavelength bandwidth light beams from a plurality of laser sources, each laser source having an output wavelength in the range of about 340 nm to about 460 nm, into a surgical beam; and optically coupling the surgical beam to a an interventional or diagnostic surgical-laser-delivery device.

A surgical process comprising: directing laser radiation to a treatment area on a tissue surface; the laser radiation consisting of a plurality of narrow-bandwidth light beams having output wavelengths in the range of 340 nm to 460 nm; wherein the laser radiation is directed to the treatment area with a surgical fiber.

BRIEF DESCRIPTION OF THE FIGURES

For a more complete understanding of the disclosure, reference should be made to the following detailed description and accompanying drawing figures wherein.

Figure 1:
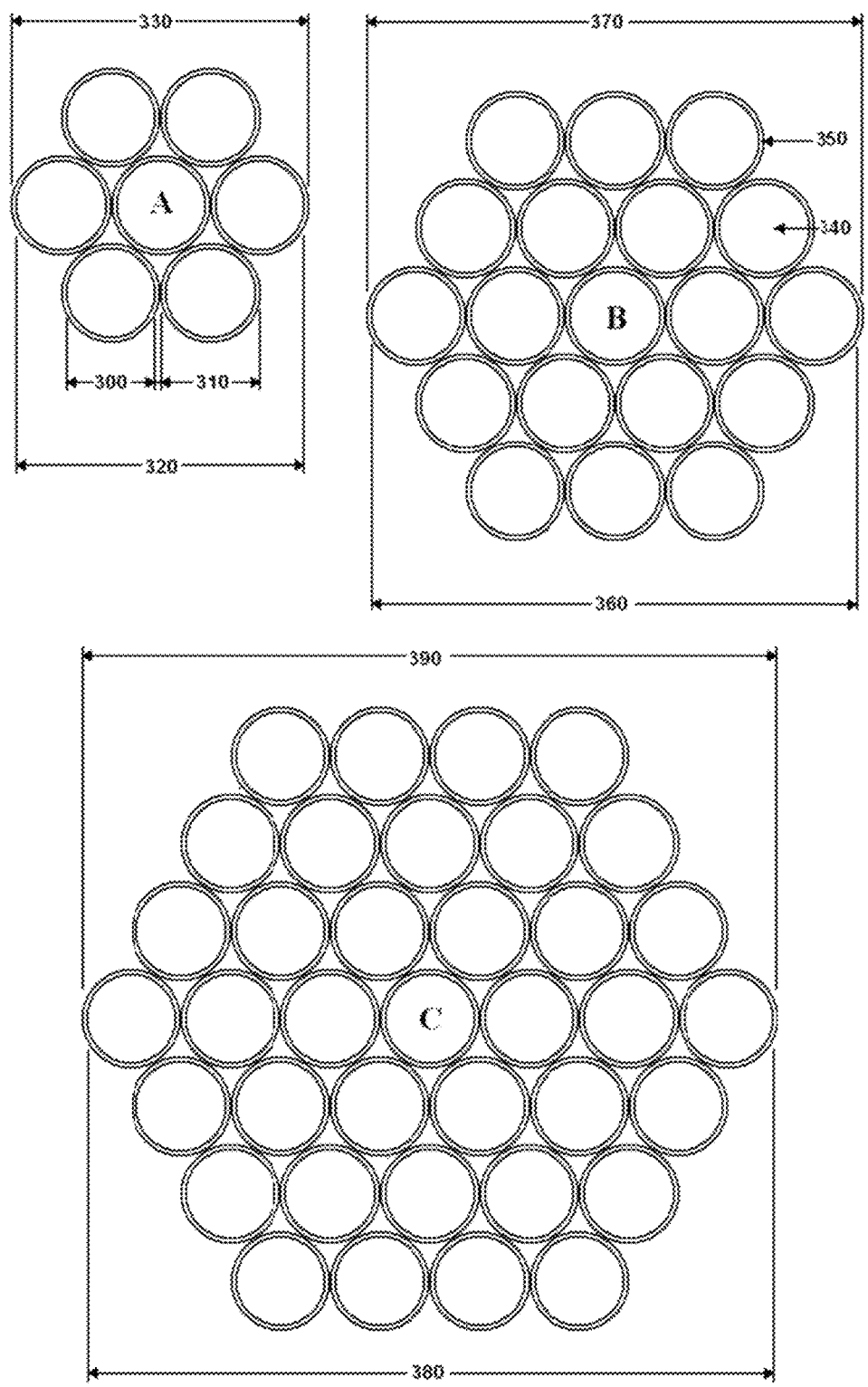
FIG. 1 includes depictions (FIGS. 1A, 1B and 1C) of the three fiber bundle terminations described for butt coupling (spatial beam combining) to surgical energy delivery fiber devices: 7 fibers, 19 fibers and 37 fibers, respectively.

While specific embodiments are illustrated in the figures, with the understanding that the disclosure is intended to be illustrative, these embodiments are not intended to limit the invention described and illustrated herein.

DETAILED DESCRIPTION

In light of the problems associated with char formation, herein is provided a surgical laser system and surgical procedure that minimizes indiscriminant absorption, scattering and collateral tissue damage. In particular, the herein provided surgical laser system and surgical procedure enable vastly improved and more durable absorption of surgical laser radiation by circumventing chromophore bleaching that is characteristic of single chromophore, single wavelength lasers, thereby minimize indirect thermal damage to adjacent and underlying tissue and further by short-circuiting char formation. That is, the system and procedure provided herein greatly reduce the conditions under which indirect thermal damage occurs in thermal transfer and eliminates indiscriminant scatter by char.

The invention described herein technically produces incoherent, polychromatic light that is a combination of a plurality of (e.g., 5, 10, 15, 20, 25, 30, 35, 40, 45, 50, 55, 60, 65, 70, 75, 80, 85, 90, 95, 100, 200, 300) of relatively low power laser light sources, each emitting high $M^2$ beam quality at wavelengths ranging from approximately 350 nm to approximately 450 nm. The discrete laser emissions (preferably low cost diode lasers) are combined in a manner or manners for best preservation of much of the high quality of the light for delivery to tissues. The wavelengths are selected for high absorption by a variety of chromophores that are present in the principal target tissue of interest, prostate tissue, many of which are also present in other target tissues of interest. In addition to targeting the chromophores themselves, the invention targets chromophore breakdown products and derivatives as well as nascent chromophores that are produced by thermal degradation and recombination of initially non-absorbing compounds, including intermediates within undesirable reaction pathways.

The invention described herein seeks to circumvent any char formation and the consequent indiscriminant absorption and coagulation of tissue that results by targeting a spectrum of chemical precursors leading to char for efficient vaporization and removal from the surgical site.

The fact that laser surgery at 532 nm, 980 nm, 2 μm or 2.1 μm is superior to the much more widely employed electrosurgical resection of hyperplasic prostate tissue (TURP) is widely accepted: with laser treatment post-operative catheterization is much shorter, hyponatremia and dysuria are far less frequent, collateral tissue damage and the post-operative complications thereof (extended catheterization, incontinence, impotence or retrograde ejaculation) are much less frequent. The surgical time required for the laser surgery is longer for large glands, but is similar to TURP in most cases. Among deterrents to broader use of lasers in treatment of the symptoms of BPH are the higher costs of equipment and consumable supplies, greater surgical skill required and longer procedure time, particularly with Ho:YAG and older, lower power KTP lasers in cases involving large glands. The latest models of 532 nm lasers (180 W) vaporize tissue at comparable rates to electrocautery (TURP) devices, but at these extreme powers the laser fibers required are larger and more costly and collateral damage risks are higher.

The costs of laser surgery are simply beyond the reach of the vast majority of the world's affected population. In order to bring laser surgery's superior outcomes to more people, the cost of the equipment and consumables must be more comparable to those required for TURP electrosurgery, or where laser outcomes become so superior as to render the choice of the inferior technique unacceptable. Surgical lasers are extremely complex and expensive devices that have become even more expensive as laser powers have increased to bring operative times in line with electrosurgery. The complex side firing fibers required for high power laser surgery are also very expensive relative to the copper wire loops used in TURP.

A fundamental thesis of this invention is that an appropriate selection of a collection of closely related wavelengths of moderate total power, produced by relatively efficient diode lasers, can provide superior and specific energy absorption to provide ablation rates on par with, or better than, high powered lasers, while reducing the costs of laser treatment so as to become economically competitive with, or superior to TURP, particularly when considering post-operative costs and complications. By identifying and targeting multiple, highly absorptive chromophores, endogenous and surgically induced, including transient chromophores representing reaction intermediates for char formation, the surgically applied light energy is more efficiently confined to vaporizing the surgical target tissue during treatment such that more tissue mass is ablated and less underlying tissue is coagulated.

Diode lasers are extremely cost effective and wall plug efficient laser sources in comparison to other laser technologies, but diode lasers have historically fared poorly in surgical applications due to poor beam quality. While admittedly a minority view, it is a thesis of this disclosure that diode lasers are now available with sufficient power at, or very near, the most advantageous wavelengths for sustained vaporization and avoidance of char formation, offering better tissue affect and concomitantly superior surgical outcomes.

In addition to the provision of optical energy at shorter wavelengths, the primary differences between the multi-wavelength surgical laser invention and prior art lasers for surgical applications are:

A—provision of a plurality of wavelengths in recognition that
    1—endogenous chromophores absorptivities are less wavelength specific than in vitro spectra for purified samples imply and these absorptivities further broaden under localized, laser-induced microenvironments, and
    2—secondary, highly absorptive chromophores with absorptive peaks separate from, but closely related to, endogenous chromophores come into existence as a result of thermally induced decomposition and recombination reactions during surgery, and
    3—the production of undesirable tissue breakdown products (char) that interfere with efficient laser energy delivery may be reduced or eliminated by targeting critical reaction pathway intermediates (such as Amadori products and melanoidines) as additional chromophores absorbing wavelengths near the peak absorptivities of the targeted endogenous and surgically induced chromophores.
B—enabling user selection of the laser output spectrum for customization of the output profile for different tissue types,
C—reducing need for high total output power allowing
    1—maintenance of superior surgical performance (reproducibility of vaporization efficiency and minimal collateral tissue coagulation) throughout a procedure,
    2—reduced thermal challenge to the fiber optic probe,
    3—enabling alternative side-firing fiber designs that have proven incompatible with high powers of modern surgical lasers,
    4—providing a capacity for delivery of full laser power through the surgical fiber probe, in air, for greatly simplified output power level calibration,
    5—enabling the use of side firing and other fiber probes in direct contact with tissues, and
    6—enabling the coupling of a disposable surgical fiber probe positions along the light path other than the instrument chassis surface, thereby reducing the cost of consumables,
D—providing exceptional beam quality by reducing the power density in the lasing elements and optics via division of the power production among a plurality of small, low power laser generators and micro-optics capable of being efficiently and uniformly cooled.

Figure 5:
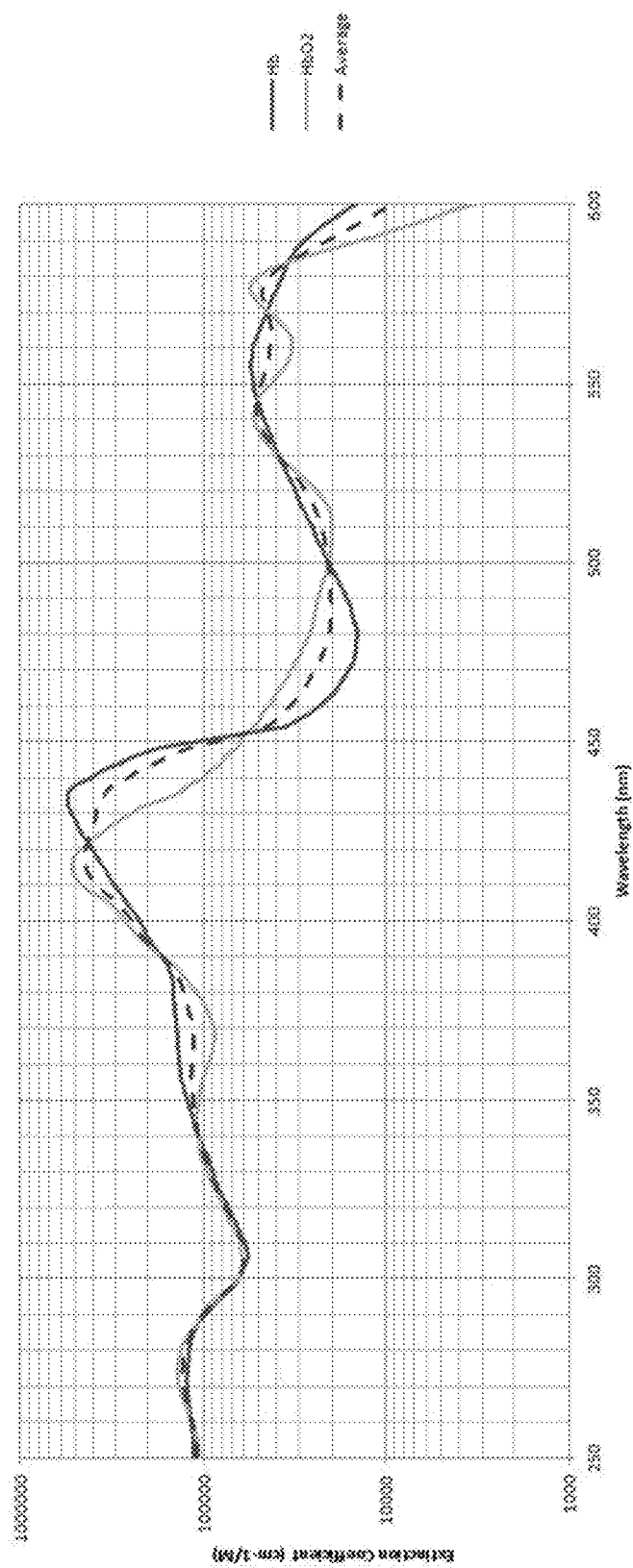
FIG. 5 is a plot of molar extinction versus wavelength for Hb, HbO2 and the average of the two curves.

KTP lasers are said to 'photoselectively' vaporize tissue due to specifically targeting $HbO_2$. $HbO_2$ does peak in absorptivity near 532 nm, in dilute solution (~545 nm) but this absorptivity is an order of magnitude less than that in the purple region of the visible spectrum (~415 nm in dilute solution). There is also considerable variation in the literature as to the location of these $HbO_2$ absorption peaks (in the mid-500 nm region and in the low 400 nm region), ranging over roughly 20 nm and likely arising from differences between matrices within which measurements were made. The molar extinction coefficients for hemoglobin (Hb) and $HbO_2$ in water at 532 nm are roughly 40,600 $cm^{-1}M^{-1}$ and 43,900 $cm^{-1}M^{-1}$, respectively (average 42,000 $cm^{-1}M^{-1}$). The molar extinction coefficients for Hb and $HbO_2$ are roughly 342,600 $cm^{-1}M^{-1}$ and 524,300 $cm^{-1}M^{-1}$ at 414 nm (average 433,440 $cm^{-1}M^{-1}$) or 552,200 $cm^{-1}M^{-1}$ and 214,100 $cm^{-1}M^{-1}$ at 432 nm (average 383,100 $cm^{-1}M^{-1}$) FIG. 5.

The above data suggest that purple light will be absorbed in a shorter path (tissue depth) than green light: the depth of penetration of a purple laser will be roughly 10-fold shallower with more of the light being strongly absorbed by blood than is the case for green light. Less penetration depth results in about a 10-fold higher concentration of heat released by inelastic collisions of the chromophores for equivalent incident power densities.

532 nm light rapidly photobleaches tissue because $HbO_2$ loses affinity for $O_2$ at elevated temperature (and lower pH, etc.). $O_2$ solubility in aqueous media also decreases with elevated temperature. The normal physiological abundance of $HbO_2$ in tissue is almost instantly disrupted (on the order of femtoseconds post exposure) shifting in favor of Hb, upon irradiation at 532 nm (purple also). This shift decreases absorptivity at 532 nm and 414 nm, but improves absorptivity at 433 nm. It follows that a source providing X/20 watts at 414 nm and X/20 watts at 433 nm will raise local tissue temperatures as rapidly as, and for longer than, X watts at 532 nm (in 10-fold less tissue volume) and X/2 watts at 414 nm with X/2 watts at 433 nm will vaporize an equivalent volume of tissue as X watts of 532 nm but will do so in $\frac{1}{10}^{th}$ the time or less and with $\frac{1}{10}^{th}$ the collateral coagulation. It also follows that, in targeting $HbO_2$ and Hb, some Hb breakdown products and derivatives thereof, the ablation performance of the purple laser will greatly exceed that predicted by absorption coefficients alone. Where total purple power and green power are equivalent, the purple power will be more rapidly, specifically and sustainably absorbed than the green: desired tissue effects will be enhanced and the undesired tissue effects will be diminished.

It is relevant to reiterate that, for the art described herein, "414 nm" and "433 nm" and such are merely reference wavelengths for chromophore maxima under very narrow, non-physiological conditions. The preferred embodiments provide multiple wavelengths near and around these reference wavelengths to target chromophores undergoing bathochromic and hypsochromic shift as well as preferentially bound alternative ligand absorptivities.

As the target chromophores are vaporized away from tissue, much of the surrounding tissue is vaporized as well (heated by inelastic collisions), but some tissue fragments remain. The remnants of tissue block clear irradiation of the underlying tissue containing more target chromophores. The more rapidly and efficiently the target chromophores are heated, the more completely the surrounding tissue components are vaporized and the less the interfering light scatter and heat conduction to underlying and adjacent tissues. The slower and less efficient the absorption, the more heat conduction to underlying and adjacent tissues occurs with the collateral coagulation damage leading to post-operative complications.

Tissues that are thermally denatured (coagulated) are bereft of blood, such that subsequent 532 nm irradiation is very poorly absorbed and scatters, generating more heat and damage to more tissues. It follows that the more rapidly and efficiently that hemoglobin containing tissue can be removed, the less the energy that is available to cause collateral tissue damage and the better the underlying layer then interacts with the newly incident light. It is therefore desirable and useful to provide at least two wavelengths, targeting the purple absorptivity maxima of both Hb and $HbO_2$ instead of a single wavelength targeting the green absorptivity of $HbO_2$, alone.

Some fraction of vaporized tissue is combusted and produces alternative ligands for Hb binding. Some of these ligands, e.g. CO and CN, have a much higher affinity for Hb than does $O_2$, binding irreversibly. Targeting absorption maxima for the more populous of these nascent, surgically induced chromophores further enhances overall absorptivity. Many absorption maxima for the alternative ligand-Hb species fall relatively close to the wavelengths for the endogenous chromophores. Adding these absorption maxima and nearby wavelengths to the laser source also targets bathochromic and hypsochromic shifted absorptivities and begins to form a continuum of relevant wavelengths within the spectral region of interest. Free heme is likely a fleeting, but relatively strong potential chromophore that may also be targeted by shorter wavelengths, broadening the spectral region of interest into the near ultraviolet (UV).

Contrary to the supposition widely repeated in the literature, and advanced in '764 and '694 for visible wavelength surgery, "a little char is good because it improves the absorption of the laser" (paraphrased), the thesis of this work is that char is always bad. Char describes the browning and blackening of the tissue surface—carbonization—but carbonization also occurs sub-surface, where energy densities are insufficient for vaporization. Between the stages of amide hydrolysis (breaking proteins' peptide bonds) and carbonization, myriad Maillard intermediates are formed, and many of these compounds adhere to the fused silica, plastics and metals used in forming laser surgical fibers (just as a hamburger patty adheres to a hot grill). These compounds absorb inefficiently at 532 nm as compared to the shorter wavelengths provided by the new art. In prior art, Maillard products "cook" further, forming carbon seeds that grow and become more and more opaque, scattering and absorbing energy that could otherwise be specifically absorbed by chromophores. Scattered incident radiation and thermal conduction to underlying tissue layers and adjacent tissues heats them to sub-vaporization temperatures, fueling more Maillard reactions in a feedback loop driving poor performance conditions. Should Mie scattering by carbon particles occur with the new art wavelengths, its onset would be slightly sooner due to the shorter wavelengths employed, but this disadvantage is more than offset by the shallower tissue penetration of the scattered radiation as compared to prior art and the short-circuiting of carbon center formation by targeting highly absorptive precursors in these reaction pathways.

Well known among cooks, Maillard reactions produce sticky products. Fried meats such as bacon readily adhere to frying pans and cooking utensils as well as adjacent bacon strips. Grilled meats adhere to the grill. Tissue under laser irradiation adheres to the optical fiber delivering that energy and the same fate befalls that tissue as the bits of hamburger that adhere to a grill: they burn to black carbon. Carbonized tissues adhering to a side firing fiber (lateral delivery fibers are the most common delivery device for laser surgery for BPH) block and absorb laser light as heat. As the temperature of the surgical fiber rises, the output window on the fiber devitrifies (rearranges from amorphous silica to high crystobalite), becoming translucent, birefringent and scattering additional laser light rather than delivering it unperturbed to the target. As temperatures continue to rise, fused silica degradation progresses to hydrolysis: the silica window dissolves along the light path and may perforate. As surgical irrigation (water) enters the protective cap, the refractive index difference critical to the redirection function of the fiber is lost and the fiber fires in the forward direction: urethral perforations, bladder neck damage and even bladder perforations have been reported.

Considerable research has been focused upon reducing the tissue adhesion problem in laser delivery fibers, particularly side firing fibers, to no avail. Organic and inorganic anti-adhesion coatings of myriad chemistries have been applied to side fire caps in hopes of forestalling adhesion. Automated motion devices have been studied and fibers incorporating overheating detection and feedback systems have been deployed. Recently, BPH fibers with internal cooling have been introduced to address the problems brought on by thermal degradation in BPH surgery. It would be desirable and useful to provide a surgical light source that reduces the occurrence and/or severity of thermal degradation in surgical fibers, proactively rather than reactively, through targeting surgically induced products that adhere to surgical fibers.

Where polarized light is not required, the methods available for combining laser sources of the same wavelength for increased power are limited to two continuous output sources (or a few sources where output is pulsed), often at some expense of $M^2$ beam quality. Closely related, non-overlapping wavelengths may be combined without significant loss in beam quality but many applications of intense light require, linear polarization, coherence or monochromatic energy, all of which are lost in multiwavelength beam combining. Coherent, monochromatic and polarized light are not required for effective surgery, but simple tissue interaction models appear to have led prior art designers to the different conclusions. Contrary to prior design optimization scenarios, a thesis herein supports claims of superior utility for multiple wavelengths if sufficient power can be safely delivered through a flexible and biocompatible fiber optic. Conveniently, multiple wavelength sources may be efficiently combined by at least three basic methods: polarization beam combining, spatial overlap and spectral beam combining (aka wavelength beam combining).

Small, low cost and very high beam quality diode laser sources now exist in the spectral region of interest for this invention, but the relatively low output powers available has deterred most designers from considering these devices for surgical applications, particularly where somewhat large masses of tissue are involved. In studying the available endogenous chromophores as well as their breakdown products and reaction products thereof, it is evident that a polychromatic, incoherent light source formed from combining a plurality of these small diode sources, in a relatively narrow spectral range, has greater utility than would a higher powered, single or dual wavelength device.

Spatial overlap is used herein to describe simple bundling of small core fibers for common launch into larger core fibers. FIGS. 1 A, B and C illustrate three such hex pack bundles of 1.1:1 CCDR fiber (CCDR is cladding 350 to core 340 diameter ratio). Lower CCDR fiber may also be considered for tighter packing, and fused hex packs are also an option affording non-hex pack bundling, e.g. a fused ring of 8 fibers becomes a pizza slice fusion termination. Sources coupled to smaller core fibers may also be used where high ratio spatial coupling is desired, but 100 µm core 300, 110 µm clad 310 fiber is the most common fiber currently used for fiber coupling of the low power diode sources of particular interest to this disclosure. The smallest core single fiber that is compatible with the hex pack bundles is defined by the diameter of the core edges of hex packed fibers: 320 µm 320 for a 7-fiber hex pack, 540 µm 360 for a 19-fiber hex pack and 760 µm 380 for a 37-fiber hex pack. For ease of alignment, however, the total diameters—330 µm 330, 550 µm 370, and 770 µm 390—are usually considered as the practical minimum.

Figure 2:
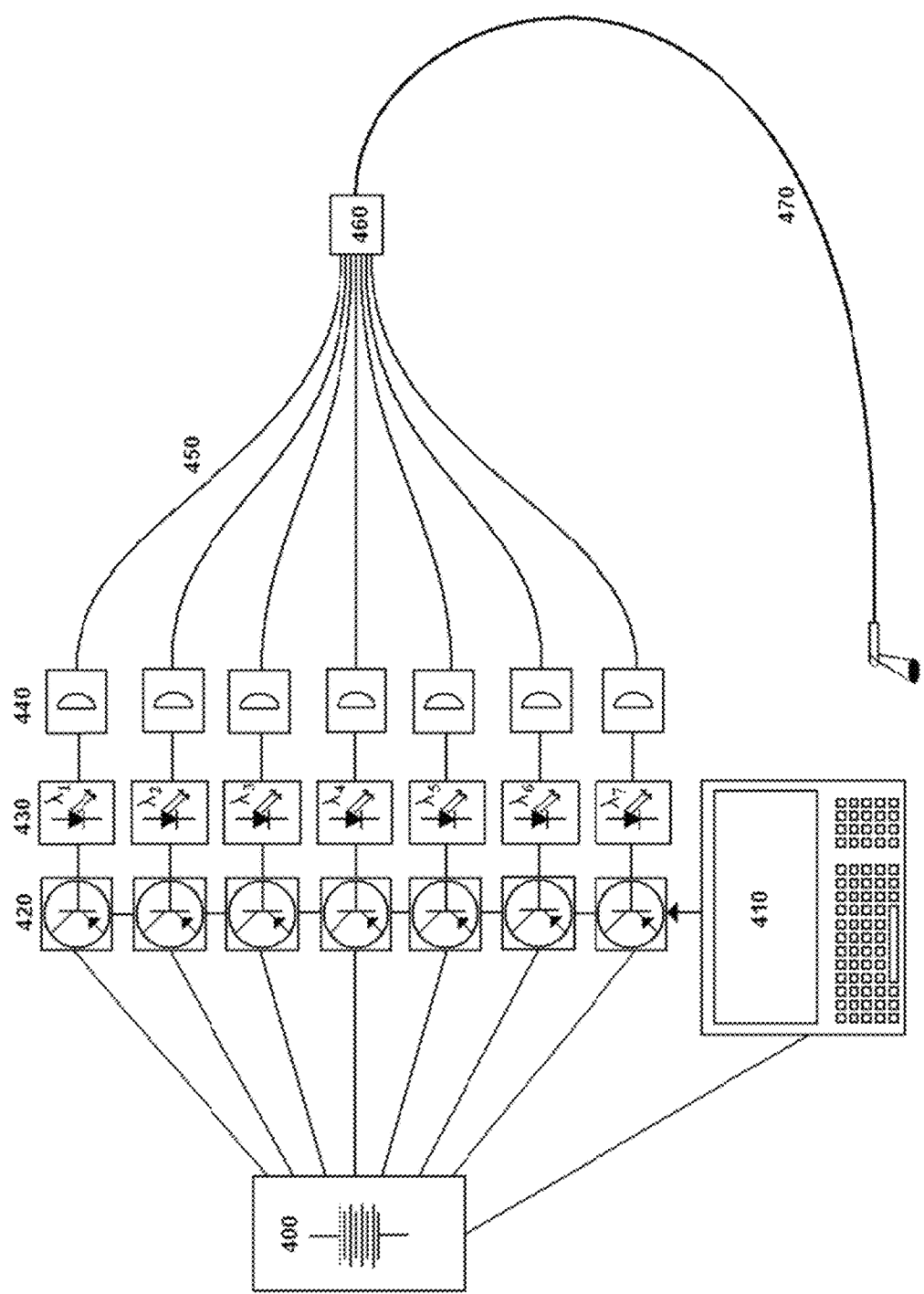
FIG. 2 is a block diagram of the simplest embodiment of the art: a 7-laser, spatially combined source.

FIG. 2 depicts a simple, 7-wavelength, spatially combined source. A power source 400 supplies individual diode drivers 420 that are controlled individually by a microcomputer (internal or external, including use of a smart phone or tablet). The drivers control the power produced by each of seven diode laser sources (λ1 through λ7) whose outputs are focused 440 onto small core optical fibers 450. The 7 fibers are bundled into a hex pack and coupled to a larger core surgical fiber 470 at 460. An advantage of this simplistic method of beam combining is that the wavelength need not be different and non-overlapping such that two or more of sources may be of the same wavelength.

In that many of the commercially available sources for wavelengths in the spectral region of interest produce relatively low power (<200 mW to 1 W), the practical maximum power for a multiwavelength laser based upon commercial diode lasers where all of the wavelengths are different and non-overlapping is less than 25 W for even a 37-fiber hex pack. By adding polarization beam combining prior to fiber coupling (horizontally polarized laser combined with a vertically polarized laser of the same wavelength by way of a polarized thin film) this power may be effectively doubled to about 50 W, but polarization beam combining is far more costly than spatial beam combining. And while coupling diodes to even smaller core fiber is a possible way to increase the total power available for coupling to surgically relevant fiber core diameters, through higher fiber count hex pack bundles, producing hex pack arrays of very small diameter fibers is technically challenging and the returns diminish with decreasing fiber diameter (because the cladding thickness minimum is determined by the wavelength, not by the core dimension). An alternative or supplementary means of beam combining would be helpful.

Spectral beam combining—also known as wavelength beam combining and incoherent beam combining—is a method of power scaling that utilizes a wavelength sensitive beam combiner: an optical element that deflects different wavelengths at different angles. Most optics do this to some extent, and a great deal of effort is expended in reducing the chromatic aberrations that result, but some optical components are designed to maximize the effect, e.g. prisms, diffraction gratings, dichroic mirrors.

For power scaling, reflective optics are more desirable than transmissive optics because they typically absorb less of the incident radiation and are more easily cooled. In separating a spectrum into its component wavelengths, a reflective diffraction grating accepts collimated light and reflects each wavelength at a slightly different angle. In the reverse, collimated outputs of different wavelengths from non-overlapping sources, directed at the diffraction grating at appropriate and slightly different angles, will combine into a single collimated, polychromatic beam. This beam may then be focused onto a target that is roughly equivalent in dimension to the sources, at the same numerical aperture as produced by the sources, i.e. there is little degradation in the $M^2$ quality of the polychromatic beam versus the individual source outputs.

Figure 3:
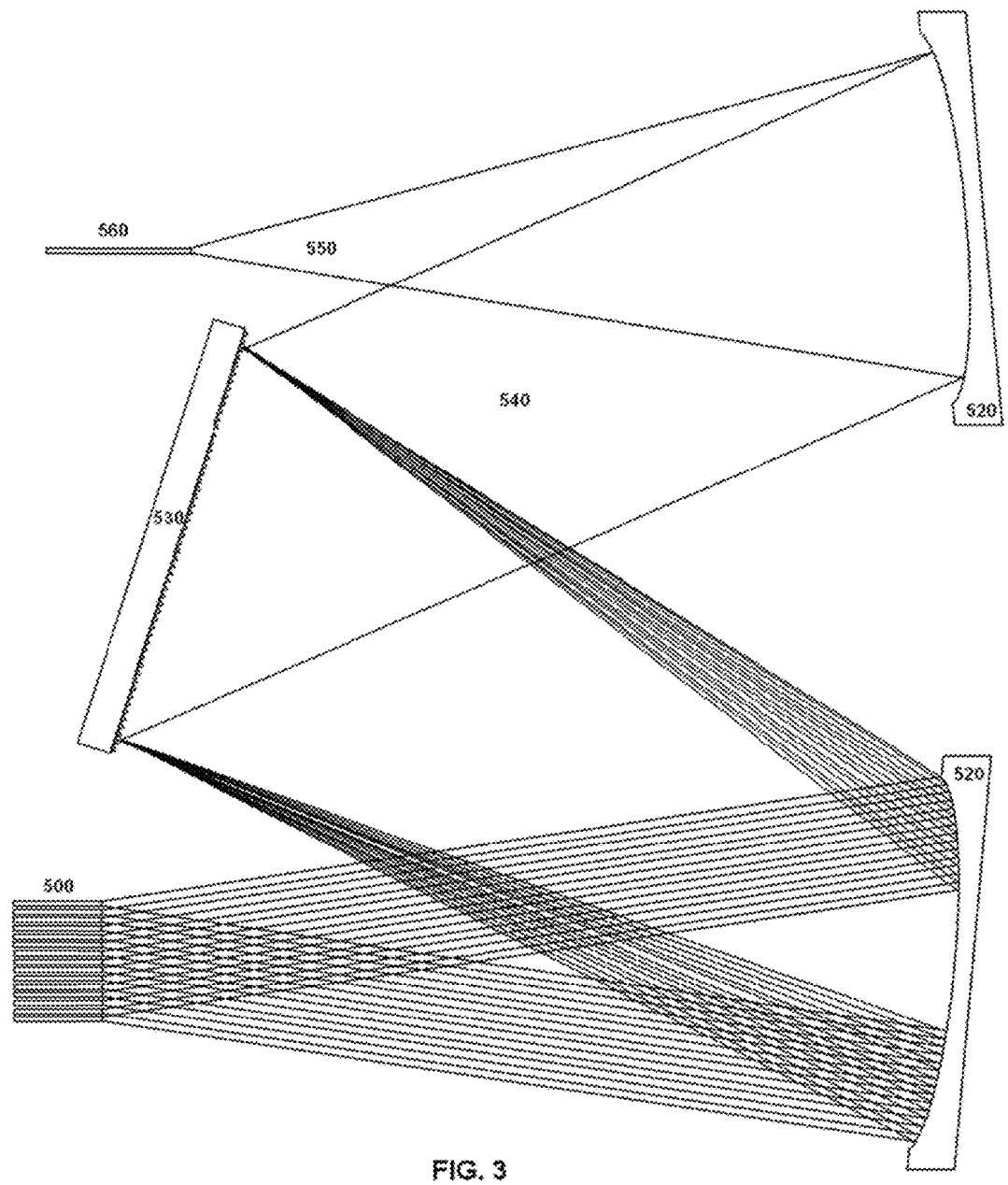
FIG. 3 depicts a simplified wavelength combining scheme using a polychromator.

FIG. 3 illustrates a spectral beam combiner of 15 sources 500 operating at different, non-overlapping wavelengths that are collimated by a highly reflective, curved mirror 520 such that the wavelengths impart the diffraction grating 530 at slightly different angles, reflecting as a single collimated beam 540 that is focused 550 onto a receiving optic 560. As with the spatial combiner, this scheme is not ideal given the spectral overlap of the available diode laser sources' wavelengths and the rather large disparity in the maximum power available at each wavelength: one cannot simply add more diodes for weaker wavelengths because no spectral overlap is permitted and diodes emitting adjacent wavelengths can overlap, forcing a selection of isolated sources for combining in a single spectral overlap beam combiner.

Figure 4:
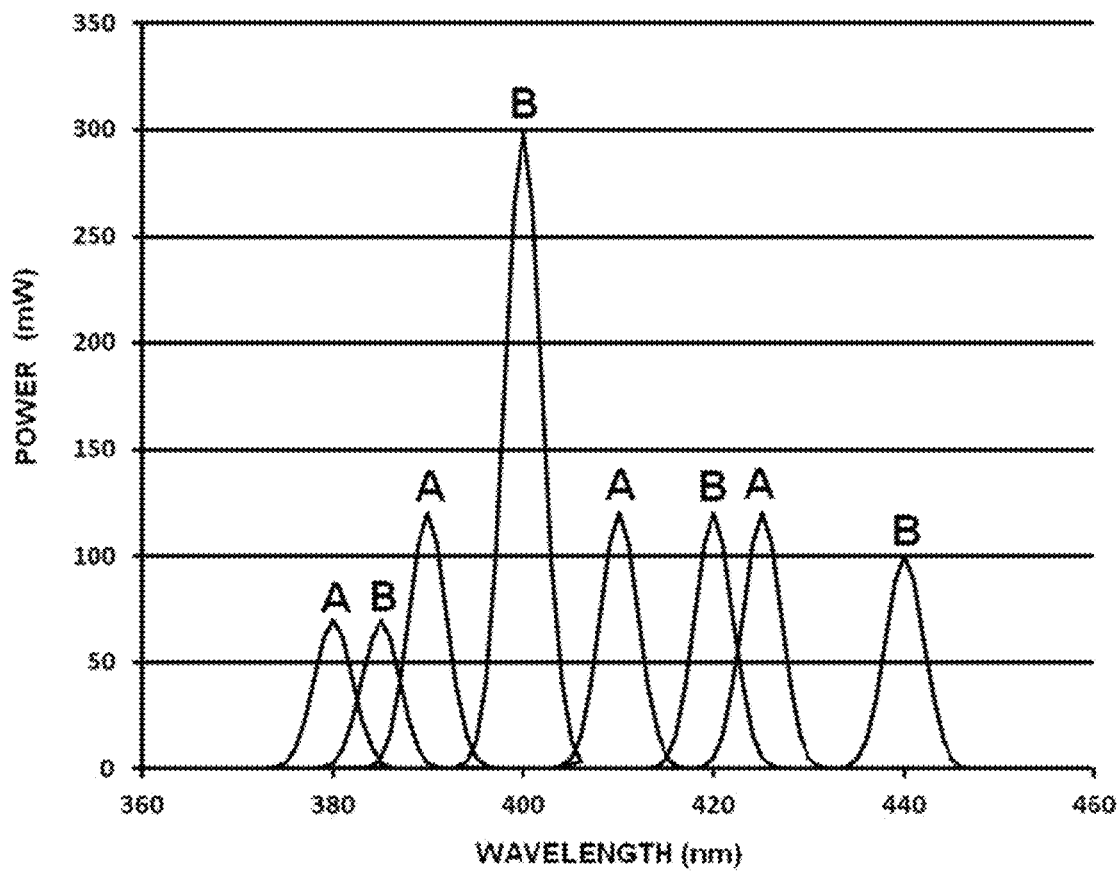
FIG. 4 depicts the outputs of diode lasers manufactured by a single firm, as of October, 2012.

The solution to the drawbacks of both beam combining schemes is to use both schemes, or where necessary all three schemes, as may be the case where laser diode sources of particularly useful wavelengths are only available at relatively low power. While the selection of wavelengths within the spectrum of interest remains relatively small, new wavelengths are regularly offered and custom wavelengths are possible given a sufficient market for them. Considering just the diode lasers available from a single manufacture FIG. 4 for illustration purposes, by combining and selecting groups of alternating wavelengths (A and B) for separate spectral beam combining, then combining these outputs spatially, a dramatic increase in output power is achieved. Where more wavelengths are used in each spectral combiner, and more of those wavelengths are polarization combined prior to spectral combining, far more power is available to feed the spatial combiner.

New diode wavelengths are being offered on a regular basis and some diode output powers within the spectral region of interest have recently risen dramatically. While some issues remain with disparate available output powers at different wavelengths, such difficulties are also diminishing. Using existing wavelengths at the current maximum available power, production of 40+W sources for 365 μm surgical delivery fibers, 100+W sources for 550 μm fibers, and 180+W sources for 760 μm fibers are possible if the design bias favors diode laser wavelengths with the highest available output powers, and/or lower power sources are polarization combined prior to spectral combining. In that a thesis of this invention is that raw power is less important than wavelength, surgical laser powers of roughly 30 W for a 365 μm surgical fiber, 80 W for a 550 μm surgical fiber and 140 W for an 800 μm surgical fiber are more realistic goals. As output powers for diode lasers increase, however, the potential for delivery of these average powers and higher are possible, and operator selection among multiple, tissue specific spectral profiles is facilitated at therapeutically relevant total power for myriad spectral output profiles.

Prostate tissue is the primary target tissue of the art disclosed herein, and prostate tissue offers unique chromophores that are targeted by the multiwavelength laser, but any highly vascular tissue is a potential target of the light source disclosed. In addition, melanin, eumelanin and breakdown products of tissues containing these pigments may also be targeted, and spectral output may be optimized for these additional tissues. Furthermore, seminal fluid absorbs light broadly between about 300 nm and 500 nm and the strongest absorption is between roughly 350 nm and 450 nm, thereby making seminal fluid another target or surgical chromophore for near UV sources within the spectral range of interest.

In one embodiment, the herein provided surgical laser system is a multiwavelength surgical tool. This multiwavelength surgical tool preferably includes a first plurality of laser sources with each laser source, individually, having an output wavelength in the range of about 340 nm to about 460 nm, preferably 380 nm to about 440 nm. Where each laser source output wavelength, individually, corresponds to an absorption maximum of a surgical chromophore in the range of about 340 nm to about 460 nm, or an environmentally shifted maximum, a derivative, breakdown product or recombination product maximum. This plurality of laser sources is preferably optically coupled to an interventional and/or diagnostic laser-delivery device (e.g., with a surgical optical fiber). In one particularly preferable instance, the laser sources consist of laser diodes, wherein the laser diodes each individually have outputs in the range of 340 nm to 460 nm. In a still more preferable instance, the laser sources include a first laser diode that has an output at about 414 nm; and a second laser diode that has an output at about 433 nm. In another instance, the surgical tool can be free of a laser source that has an output above about 500 nm. In yet another instance, the output wavelengths differ by at least 2 nm. In a particularly preferable example, the surgical laser system includes a plurality of laser sources (e.g., diodes) that have the same output wavelength (e.g. a first plurality of laser diodes having an output wavelength at about 350 nm, a second plurality of laser diodes having an output wavelength at about 370 nm, a third plurality of laser diodes having an output wavelength at about 390 nm, a fourth plurality of laser diodes having an output wavelength at about 410 nm, a fifth plurality of laser diodes having an output wavelength at about 430 nm, and/or a sixth plurality of laser diodes having an output wavelength at about 450 nm). Still further, the surgical laser system can have a plurality of a plurality of laser diodes having polarization combined outputs (e.g., 10, 20, 30, 40, 50, or 60 pairs of laser diodes). The combined outputs coupled to a first fiber which can be collected into a bundle and then coupled to a surgical fiber. Notably, the surgical laser system can include single laser diodes and pluralities of laser diodes where the groupings are distinguished based on the output wavelengths.

Preferably, the absorption maximum of the surgical chromophore is selected from the absorption peaks, the bathochromic shifts, and hypochromic shifts of in vivo materials. In one instance, the in vivo materials can be selected from an endogenous chromophore, a thermal degradation product thereof; a light-induced chromophore variant, a thermal degradation product thereof; a recombinant product thereof; and a mixture thereof. In one particularly preferable instance, the in vivo materials include both deoxy-hemoglobin and oxyhemoglobin.

In one example, the surgical tool additionally includes a plurality of optical fibers, each optical fiber individually optically coupled to a laser source with these optical fibers terminating as a bundle. The bundle is preferably optically coupled to the surgical-laser-delivery device. In one instance, the bundle includes a hex pack of seven optical fibers; a hex pack of nineteen optical fibers; or a hex pack of thirty seven optical fibers.

In another example, the surgical tool additionally includes a beam combiner optically coupled to the laser sources with the beam combiner optically coupled to the surgical-laser-delivery device. For example, the beam combiner can be selected from the group consisting of a polarization beam combiner, a spectral beam combiner, and a mixture thereof. In another example, the beam combination can include polarization, spectral and spatial (fiber bundle) beam combination.

In one particularly useful example, the surgical laser system can include about 30, 40, 50, or 60 pairs of polarization combined laser diodes (e.g., 60 pairs with output wavelengths that differ by 2 nm). The polarization combined output beams coupled to, for example, a 100 µm fiber. A plurality of these fibers collected into a bundle and coupled to a surgical fiber. In one instance, the total output of the surgical fiber can be or exceed about one kilowatt. In one instance, the surgical laser system can include singlets (1), pairs (2), trios (3), quartets (4), quintets (5), sextets (6), septets (7), octets (8), nonets (9), and/or deculpets (10) of laser diodes.

Another embodiment is a surgical process that includes combining a plurality of narrow-bandwidth light beams from a plurality of laser sources, each laser source having an output wavelength in the range of about 340 nm to about 460 nm, into a surgical beam; and optically coupling the surgical beam to an interventional or diagnostic laser-delivery device. Preferably, the surgical process further includes emitting the surgical beam from the surgical-laser-delivery device; and delivering the surgical beam to a target tissue. In one example, the surgical process includes output wavelengths which correspond to absorption maxima of one or more surgical chromophore in the range of about 340 nm to about 460 nm. Preferably, the absorption maximum of a surgical chromophore is selected from the absorption peaks, the bathochromic shifts, and hypochromic shifts of in vivo materials, where the in vivo materials are selected from an endogenous chromophore, a thermal degradation product thereof; a light-induced chromophore variant, a thermal degradation product thereof; and a recombinant product thereof; and a mixture thereof.

Still another embodiment is a surgical process that includes directing laser radiation to a treatment area on a tissue surface, the laser radiation consisting of a plurality of narrow-bandwidth light beams having output wavelengths in the range of 340 nm to 460 nm. Preferably, the laser radiation is directed to the treatment area with a surgical fiber. In one instance, the surgical process includes providing the laser radiation from a plurality of laser diodes, each laser diode, individually, emitting light at a wavelength in the range of about 340 nm to about 460 nm; and combining the emitted light into the surgical fiber. In another instance, the surgical process includes ablating the tissue surface with the laser radiation without charring the tissue surface. Notably, the surgical process embodiments and features thereof can be combined.

What is claimed:

1. A process comprising:
    combining light beams from a plurality of laser sources into a polychromatic light beam that comprises a plurality of narrow-bandwidth light beams having output wavelengths in the range of 340 nm to 460 nm;
    the plurality of laser sources including a first-laser source and a second-laser source, the first-laser source and the second-laser source having output wavelengths which differ by at least 2 nm; and
    optically coupling the polychromatic light beam to an interventional or diagnostic-laser-delivery device adapted for directing the polychromatic light beam to a surgical target.

2. The process of claim 1, wherein combining the beams from the plurality of laser sources includes a waveguide optically coupled to a first laser source and a second laser source.

3. The process of claim 2, wherein the first laser source is a continuous wave laser source.

4. The process of claim 1, further comprising directing the polychromatic light beam to a surgical target; and
    vaporizing the surgical target without char formation.

5. The process of claim 4, where in the surgical target is hyperplastic prostate tissue.

6. The process of claim 4, where in the surgical target is soft tissue.

7. The process of claim 1 further comprising:
    directing the polychromatic light beam from the delivery device to a surgical target;
    contacting the surgical target with the polychromatic light beam, wherein the first-laser source output wavelength corresponds to a first absorption maximum of a surgical chromophore, and the second-laser source output wavelength corresponds to a second absorption maximum of a surgical chromophore.

8. The process of claim 7, wherein the polychromatic light beam vaporizes the surgical target without char formation.

9. The process of claim 7, further comprising a third-laser source having a third-laser source output wavelength; wherein the polychromatic light beam includes the third-laser source output wavelength which corresponds to a third absorption maximum of a surgical chromophore.

10. The process of claim 7, wherein the delivery device includes an optical fiber; and wherein the polychromatic light beam is coupled to the optical fiber.

11. The process of claim 7, wherein the surgical target includes a first surgical chromophore and a second surgical chromophore; and wherein the first output wavelength corresponds to an absorption maximum of the first surgical chromophore, and the second output wavelength corresponds to an absorption maximum of the second surgical chromophore; wherein the surgical chromophores are, individually, selected from an endogenous chromophore, a chromophore breakdown product, or a chromophore derivative.

12. A process comprising:
   combining light beams from a plurality of diode laser sources into a polychromatic light beam;
   the plurality of diode laser sources including a first-laser source and a second-laser source, the first-laser source and the second-laser source having output wavelengths which differ by at least 2 nm and are in the range of about 340 nm to about 460 nm;
   optically coupling the polychromatic light beam to an interventional or diagnostic-laser-delivery device;
   directing the polychromatic light beam from the delivery device to a surgical target;
   contacting the surgical target tissue with the polychromatic light beam; and
   vaporizing the surgical target tissue.

13. The process of claim 12, wherein each diode laser source has a power output less than about 1 W.

14. The process of claim 12, wherein the first-laser source has an output wavelength which corresponds to an absorption maximum of deoxy-hemoglobin in the range of about 340 nm to about 460 nm; and the second-laser source has an output wavelength which corresponds to an absorption maximum of oxy-hemoglobin in the range of about 340 nm to about 460 nm.

15. The process of claim 12, wherein the surgical target is selected from soft tissue, prostate tissue, seminal fluid, and a mixture thereof.

16. The process of claim 12, wherein the first laser source has a first output wavelength which corresponds to an absorption maximum of a tissue endogenous chromophore, and the second laser source has a second output wavelength which corresponds to an absorption maximum of a second endogenous chromophore, a chromophore breakdown product, or a chromophore derivative.

* * * * *